US009442095B2

(12) United States Patent
Jiao et al.

(10) Patent No.: US 9,442,095 B2
(45) Date of Patent: Sep. 13, 2016

(54) OPTICAL COHERENCE PHOTOACOUSTIC MICROSCOPY (75) Inventors: Shuliang Jiao, Los Angeles, CA (US); Hao Zhang, Evanston, IL (US)

(73) Assignees: NORTHWESTERN UNIVERSITY, Evanston, IL (US); UNIVERSITY OF SOUTHERN CALIFORNIA, Los Angeles, CA (US)

( * ) Notice: Subject to any disclaimer, the term of this patent is extended or adjusted under 35 U.S.C. 154(b) by 562 days.

(21) Appl. No.: 13/524,813

(22) Filed: Jun. 15, 2012

(65) Prior Publication Data

US 2012/0320368 A1    Dec. 20, 2012

Related U.S. Application Data (60) Provisional application No. 61/497,323, filed on Jun. 15, 2011.

(51) Int. Cl.
*G01B 9/02* (2006.01)
*G01B 17/00* (2006.01)
*G01N 29/06* (2006.01)

(52) U.S. Cl.
CPC ......... *G01N 29/0681* (2013.01); *G01B 9/0203* (2013.01); *G01B 9/02091* (2013.01)

(58) Field of Classification Search
CPC ....................... G01B 9/02091; G01N 29/2418
See application file for complete search history.

(56) References Cited

U.S. PATENT DOCUMENTS 4,267,732 A    5/1981 Quate
4,740,081 A * 4/1988 Martens et al. ............. 356/479
4,764,005 A    8/1988 Webb et al.
5,062,297 A    11/1991 Hashimoto et al.
5,196,006 A    3/1993 Klopotek et al.
(Continued)

FOREIGN PATENT DOCUMENTS

WO    WO 2007/035934    3/2007
WO    WO 2010/107930    9/2010
WO    WO 2010/107933    9/2010

OTHER PUBLICATIONS

PCT/US2012/042724 International Search Report and Written Opinion date mailed Sep. 7, 2012, (12 pages).
(Continued)

*Primary Examiner* — Kara E Geisel
*Assistant Examiner* — Dominic J Bologna
(74) *Attorney, Agent, or Firm* — Hanley, Flight and Zimmerman, LLC (57) ABSTRACT A system and method for providing an optical coherence photoacoustic (OC-PAM) microscopy. An OC-PAM microscope includes a light source that outputs light, a scanner, a detector, a transducer, and an image processing module. The scanner receives the light and scans the light across a sample. The detector receives reflected light from the sample in response to the scanned light. The transducer detects photoacoustic waves induced in the sample by the scanned light. The image processing module receives output from the detector and the transducer and generates a photoacoustic microscopy (PAM) image and an optical coherence tomography (OCT) image based on the received output from the detector and the transducer. The PAM and OCT image data may be fused to form a single, OC-PAM image. Additionally, a series of PAM images and OCT images, respectively, may be combined to generate three-dimensional PAM and OCT images, respectively.

30 Claims, 7 Drawing Sheets

(56) References Cited

U.S. PATENT DOCUMENTS

| | | | |
|---|---|---|---|
| 5,521,657 A | 5/1996 | Klopotek | |
| 5,557,352 A | 9/1996 | Nordquist | |
| 5,562,095 A | 10/1996 | Downey et al. | |
| 5,784,152 A * | 7/1998 | Heffelfinger et al. | 356/73 |
| 5,829,439 A | 11/1998 | Yokosawa et al. | |
| 5,840,023 A | 11/1998 | Oraevsky et al. | |
| 6,309,352 B1 | 10/2001 | Oraevsky et al. | |
| 6,423,001 B1 | 7/2002 | Abreu | |
| 6,652,459 B2 | 11/2003 | Payne et al. | |
| 6,671,043 B1 | 12/2003 | Huettman | |
| 6,849,210 B2 | 2/2005 | Bothe et al. | |
| 6,979,292 B2 | 12/2005 | Kanayama et al. | |
| 7,404,637 B2 | 7/2008 | Miller et al. | |
| 8,016,419 B2 | 9/2011 | Zhang et al. | |
| 8,025,406 B2 | 9/2011 | Zhang et al. | |
| 2001/0014060 A1* | 8/2001 | Freeman et al. | 369/44.23 |
| 2005/0070803 A1 | 3/2005 | Cullum et al. | |
| 2006/0055936 A1* | 3/2006 | Yun et al. | 356/479 |
| 2006/0184042 A1 | 8/2006 | Wang et al. | |
| 2007/0276269 A1* | 11/2007 | Yun et al. | 600/504 |
| 2007/0299341 A1 | 12/2007 | Wang et al. | |
| 2008/0033262 A1 | 2/2008 | Peyman et al. | |
| 2008/0088838 A1 | 4/2008 | Raicu et al. | |
| 2008/0123083 A1* | 5/2008 | Wang et al. | 356/73 |
| 2009/0086213 A1* | 4/2009 | Masuda | 356/479 |
| 2010/0245766 A1 | 9/2010 | Zhang et al. | |
| 2010/0245769 A1 | 9/2010 | Zhang et al. | |
| 2010/0245770 A1 | 9/2010 | Zhang et al. | |
| 2010/0249562 A1* | 9/2010 | Zhang | A61B 5/0059 600/365 |
| 2010/0268042 A1 | 10/2010 | Wang et al. | |
| 2012/0062841 A1 | 3/2012 | Stetson et al. | |

OTHER PUBLICATIONS

Aiello, L.P., "Angigenic Pathways in Diabetic Retinopahy", New England Journal of Medicine 353, 839-841 (2005).
Avery, R.L. et al, "Intravitreal Bevacizumab (Avastin) in the Treatment of Proliferative Diabetic Retinopathy", Ophthalmology 113, 1695 e1-15 (2006).
Biallosterski, C., et al., "Decreased Optical Coherence Tomography-Measured Pericentral Retinal Thickness in Patients with Diabetes Mellitus Type 1 with Minimal Diabetic Retinopathy" Brit J Opthalmol 91, 1135-1138 (2007).
Barker, J.H. et al., "The hairless mouse ear for in vivo studies of skin microcirculation," Plast. Reconstr. Surg. 83, 948-959 (1989).
Booth, M.J. et al., "Adaptive aberration correction in a confocal microscope," Proceedings of the National Academy of Sciences (2002) 99(9):5788-5792.
Boppart, S.A. et al., "High-Resolution Optical Coherence Tomography-Guided Laser Ablation of Surgical Tissue", J. Surgical Research 82, 275-284 (1999).
Bower, B.A. et al., "Real-Time Spectral Domain Doppler Optical Coherence Tomography and Investigation of Human Retinal Vessel Autoregulation", J. Biomed. Opt. 12, 2007.
Cai, J. et al., "The Pathogenesis of Diabetic Retinopathy: Old Concepts and New Questions," Eye 16, 242-260 (2002).
Ciulla, T.A. et al., "Diabetic Retinopathy and Diabetic Macular Edema—Pathophysiology, Screening, and Novel Therapies", Diabetes Care 26, 2653-2664 (2003).
Cunha-Vaz, J.G., "Diabetic Retinopathy: Surrogate Outcomes for Durg Development for Diabetic Retinopathy", Ophthalmologica 214, 377-380 (2000).
Dabbs, T. et al., "Fiber-optic confocal microscope: FOCON," Applied Optics 31, 3030-3035 (1992).
De La Zerda, A. et al., "Photoacoustic Imaging of the Eye for Improved Disease Detection", Presentation No. 0043, Scientific Session 1: Emerging Optical and Optoacoustic Technologies, Sep. 24, 2009.
De La Zerda, A. et al., "Photoacoustic Ocular Imaging", Optics Letters, vol. 35, No. 3, pp. 270-272, Feb. 1, 2010.
De La Zerda, A., et al., "Carbon Nanotubes as Photoacoustic Molecular Imaging Agents in Living Mice," Nature Nanotechnology 3, 557-562 (2008).
Delori, F.C. et al., "Monochromatic Ophthalmoscopy and Fundus Photography," Arch. Ophthalmol. 5, 861-868 (1977).
Denninghoff, K.R. et al., "Retinal Imaging Techniques in Diabetes", Diatetes Tech. & Therap. 2, 111-113 (2000).
Fercher, A.F., et al., "Measurement of Intraocular Distances by Backscattering Spectral Interferometry," Optics Communications 117, 43-48 (1995).
Ferris, F. "Early Photocoagulation in Patients with Either Type I or Type II Diabetes", Trans Am Ophthalmol Soc. 94, 505-537 (1996).
Ferris, F.L. et al., "Treatment of Diabetic Retinopathy", New Engl. J. Med. 341, 667-678 (1999).
Freeman, W.R. et al., "Simultaneous Indocyanine Green and Fluorescein Angiography Using a Confocal Scanning Laser Ophthalmoscope", Archives of Ophthalmology 116, 455-463 (1998).
Fujioka, S. et al., "Correlation Between Higher Blood Flow Velocity in the Central Retinal Vein than in the Central Retinal Artery and Severity of Nonproliferative Diabetic Retinopathy", Japanese Journal of Ophthalmology 50, 312-317, 2006.
Geisen, P. et al., "Neutralizing Antibody to VEGF Reduces Intravitreous Neovascularization and may Not Interfere with Ongoing Intraretinal Vascularization in a Rat Model of Retinopathy of Prematurity", Mol Vis. 14, 354-357, 2008.
Girkin, J.M. "Adaptive optics for deeper imaging of biological samples," Curr. Opin. Biotech. (2009) 20:106-110.
Goebel, W. et al., "Retinal Thickness in Diabetic Retinopathy—Comparison of Optical Coherence Tomography, the Retinal Thickness Analyzer, and Fundus Photography", Retina—J Ret Vit Dis 26, 49-57 (2006).
Guan, K. et al., "Retinal hemodynamics in Early Diabetic Macular Edema", Diabetes 55, 813-818 (2006).
Hammer, M. et al., "Light Paths in Retinal Oximetry," IEEE Trans. Biomed. Eng. 48, 592-598 (2001).
Hammes, H.P. et al., "Pericytes and the Pathogenesis of Diabetic Retinopathy", Diabetes 51, 3107-3112 (2002).
Harris, A., et al., "A Review of Methods for Human Retinal Oximetry," Ophthalmic Surg. Lasers Imaging 34, 152-164 (2003).
Hu, S. et al., "Labelfree photoacoustic ophthalmic angiography," Optics Lett. (2010) 35(1):1-3.
Hu, S. et al., "Photoacoustic imaging and characterization of the microvasculature," J. of Biomed. Opt., 2010, vol. 15, pp. 011101-15.
Huang, C.C. et al., "Determining the Acoustic Properties of the Lens Using a High Frequency Ultrasonic Needle Transducer", Ultrasound in Medicine & Biology 33, 1971-1977 (2007).
Huang, D. et al., "Optical Coherence Tomography," Science 254, 1178-1181 (1991).
Jiang, J. et al , "Inhibition of Retinal Neovascularization by Gene Transfer of Small Interfering RNA Targeting HIF-1Alpha and VEGF", J Cell Physiol 218, 66-74, 2009.
Jiao, S. et al., "Integrated Photoacoustic Microscopy and Fiber-Optic Confocal Microscopy Using a Signal Laser Source" Proceedings of ASA BIOMED, Miami, FL (2010).
Jiao, S. et al., "Photoacoustic Ophthalmoscopy for in vivo Retinal Imaging", Optics Express 18, 3967-3972 (2010).
Jiao, S. et al., "Polarization Effect on the Depth Resolution of Optical Tomography", J. Biomed. Opt. 13, JBO Letters 060503-1 (2008).
Jiao, S. et al., "Simultaneous Acquisition of Sectional and Fundus Ophthalmic Images with Spectral-Domain Optical Coherence Tomography," Optics Express 13, 444-452 (2005). http://www.opticsinfobase.org/abstract.cfm?URI=oe-13-2-444.
Jiao, S. et al., "Simultaneous Multimodal Imaging with Integrated Photoacoustic Microscopy and Optical Coherence Tomography," Optics Letters, vol. 34, No. 19, pp. 2961-2963 (2009).
Kempen, J.H. et al., "The Prevalence of Diabetic Ritinopathy Among Adults in the United States", Arch Ophthalmol.-Chic 122, pp. 552-563 (2004).
Kern, T.S. et al., "Animal Models of Diabetic Retinopathy", Retinal and Choroidal Angiogenesis, 81-102 (2008).

(56) References Cited

OTHER PUBLICATIONS

Khoobehi, B. et al., "Hyperspectral Imaging for Measurement of Oxygen Saturation in the Optic Nerve Head", Invest. Ophthalmol. Vis. Sci. 45, 1464-1472 (2004).
Kolkman, R.G.M. et al., "In vivo Photoacoustic Imaging of Blood Vessels using an Extreme-Narrow Aperture Sensor", IEEE J Sel Top Quant 9, 343-346 (2003).
Kong, F. et al., "High-resolution photoacoustic imaging with focused laser and ultrasonic beams," Appl. Phys. Lett. (2009) 94.
Lang, G.E., "Optical Coherence Tomography Findings in Diabetic Retinopathy", Developments in Ophthalmology 39, 31-47 (2007).
Laser Institute of America, American National Standard for Safe Use of Lasers ANSI Z136.1-2007. (American National Standards Institute Inc., New York, NY, 2007).
Laufer, J. et al., "Three-Dimensional Noninvasive Imaging of the Vasculature in the Mouse Brain Using a High Resolution Photoacoustic Scanner," Applied Optics 48, D299-D306 (2009).
Li, L. et al., "Three-dimensional combined photoacoustic and optical coherence microscopy for in vivo microcirculation studies," Optics Exp. (2009) 17(19):16450-16455.
Lorenzi, M. et al., "Retinal Haemodynamics in Individuals with Well-Controlled Type 1 Diabetes", Diabetologia 51, 361-364, 2008.
Lutty, G.A. et al., Proceedings of the Third International Symposium on Retinopathy of Prematurity: An Update on ROP from the Lab to the Nursery (Nov. 2003, Anaheim, California). Mol Vis. 23, 532-580 (2006).
Mackinnon, J.R. et al., "Colour Doppler Imaging of the Ocular Circulation in Diabetic Retinopathy", Acta Ophthalmologica Scandinavica 78, 386-389, 2000.
Mannino, G. et al., "Ultrasound Biomicroscopy of the Peripheral Retina and the Ciliary Body in Degenerative Retinoschisis Associated with Pars Plana Systs", British Journal of Ophthalmology 85, 976-982 (2001).
Marsh, P.N. et al., "Practical implementation of adaptive optics in multiphoton microscopy," Optics Express (2003) 11(10):1123-1130.
Maslov, K. et al., "Effects of Wavelength-Dependent Fluence Attenuation on the Noninvasive Photoacoustic Imaging of Hemoglobin Oxygen Saturation in Subcutaneous Vasculature in vivo", Inverse Problems 23, S113-S122 (2007).
Maslov, K. et al., "Optical-Resolution Photoacoustic Microscopy for in vivo Imaging of Single Capillaires," Optics Letters 33, 929-931 (2008).
Mendivil, A., et al., "Ocular Blood Flow Velocites in Patients with Proliferative Diabetic Retinopathy and Healthy Volunteers: A Prospective Study", Br J Ophthalmol 79, 413, 1995.
Molecular Expressions, Optical Microscopy Primer, Introduction to Optical Imaging, and Photomicrography, available online at: <http://micro.magnet.fsu.edu/primer/index.html>.
Nassif, N.A. et al., "In vivo High-Resolution Video-Rate Spectral-Domain Optical Coherence Tomography of the Human Retina and Optic Nerve," Optics Express, vol. 12, No. 3, pp. 367-376, 2004.
Olson, J.A. et al., "A Comparitive Evaluation of Digital Imaging, Retinal Photography and Optometrist Examination in Screening for Diabetic Retinopathy", Diabet. Med. 20, 528-34 (2003).
Oraevsky, A.A., et al., "Optoacoustic Tomography", Biomedical Photonics Handbook, vol. PM125, pp. 1-34 (CRC Press, Boca Raton, FL, 2003).
Patil, C.A. et al., "Combined Raman Spectroscopy and Optical Coherence Tomography Device for Tissue Characterization", Optics Letters 33, 1135 (2008).
Pavlin, C.J. et al., "Ultrasound Biomicroscopy High-Frequency Ultrasound Imaging of the Eye at Microscopic Resolution", Radiol, Clin. North. Am. 36, 1047-1058 (1998).
Pechan, P. et al., "Novel Anti-VEGF Chimeric Molecules Delivered by AAV Vectors for Inhibition of Retinal Neovascularization", Gene Ther 16, 10-16 (2009).
Penn, J.S. et al., "Exposure to Alternating Hypoxia Causes Severe Proliferative Retinopathy in the Newborn Rat", Pediatr Res 36, 724-731 (1994).
Penn, J.S. et al., "Fluorescein Angiography as a Means of Assessing Retinal Vascular Pathologogy in Oxygen-Exposed Newborn Rats", Curr Eye Res. 12, 561-570 (1993).
Penn, J.S. et al., "The Range of PaO2 Variation Determines the Severity of Oxygen-Induced Retinopathy in Newborn Rats", Invest Ophthalmol Vis Sci. 36, 2063-2070 (1995).
Prahl, S., "Optical absorption of hemoglobin," SAP (Dec. 15, 1999).
Rao, B. et al., "Hybrid-scanning optical-resolution photoacoustic microscopy for in vivo vasculature imaging," Optics Lett. (2010) 35(10):1521-1523.
Ren, H.W. et al., "Imaging and Quantifying Transverse Flow Velocity with the Doppler Bandwidth in a Phase-Resolved Functional Optical Coherence Tomography", Opt Lett 27, 409-411 (2002).
Ricci, B., "Oxygen-Induced Retinopathy in the Rat Model", Doc Ophthalmol 74, 171-177 (1990).
Ruggeri, M. et al., "In vivo Three-Dimensional High-Resolution Imaging of Rodent Retina with Spectral-Domain Optical Coherence Tomography," Investigative Opthalmology & Visual Science 48, 1808-1814 (2007).
Ruggeri, M. et al., "Quantitative evaluation of retinal tumor volume in mouse model of retinoblastoma by using ultra high-resolution optical coherence tomography," J. Innov. In Optical Health Sci. (2008) 1(1):1-12.
Ruggeri, M. et al., "Retinal structure of birds of prey revealed by ultra-high resolution spectral-domain optical coherence tomography," IOVS Papers in Press, Macuscript iovs 10-5633 (Jun. 16, 2010).
Schmitz-Valckenberg, S. et al., "Evaluation of Autofluorescence Imaging with the Scanning Laser Ophthalmoscope and the Fundus Camera in Agerelated Geographic Atrophy," American Journal of Ophthalmology 146, 183-192 (2008).
Sharp, P. et al., "The Scanning Laser Ophthalmoscope—A Review of its Role in Bioscience and Medicine", Phys Med Biol. 49, 1085-96 (2004).
Sherman, L. et al., "Adaptive correction of depth-induced aberrations in multiphoton scanning microscopy using a deformable mirror," J. Microscopy (2002) 206(1):65-71.
Shung, K.K. et al., "Piezoelectric Materials for High Frequency Medical Imaging Applications: A Review", Journal of Electronic Ceramic 19, 139-145 (2007).
Silverman, R. et al., "Fine-resolution photoacoustic imaging of the eye," Proceedings of SPIE (2010) 7564.
Sivaramakrishnan, M. et al., "Limitations of Quantitative Photoacoustic Measurement of Blood Oxygenation in Small Vessels", Phys. Med. Biol. 52, 1349-1361 (2007).
Smith, L.E.H. et al., "Oxygen-induced retinopathy in the mouse," Inv. Ophthal. Vis. Sci. (1994) 35(1):101-111.
So et al., "Two-photon deep tissue ex vivo imaging of mouse dermal and subcutaneous structures," Optics Express 3, 340 (1998).
Song, K.H. et al., "Near-Infrared Gold Nanocages as a New Class of Tracers for Photoacoustic Sentinel Lymph Node Mapping on a Rat Model," Nano Letters 9, 183-188 (2009).
Strauss, O., "The Retinal Pigment Epithelium in Visual Function," Physiol. Rev. 85, 845-881 (2005).
Tang, S. et al., "Imaging Subcellular Scattering Contrast by Using Combined Optical Coherence and multiphoton Microscopy", Journal of Biomedical Optics 11, 020502 (2006).
Trick, G.L. et al., "Early Supernormal Retinal Oxygenation Response in Patients with Diabetes", Invest. Ophthalmol. Vis. Sci. 47, 1612-1619 (2006).
Ushio-Fukai, M. et al., "Reactive species and angiogenesis—NADPH oxidase as target for cancer therapy," Cancer Lett. (2008) 266(1):37-52.
Van Bijsterveld, O.P., Diabetic Retinopathy, Chapter 13—Histopathology and Pathophysiology of Diabetic Retinopathy, Martin Dunitz (2000).
Van Dijk, H.W. et al., "Selective loss of inner retinal layer thickness in type I diabetic patients with minimal diabetic retinopathy," Inv. Ophthal. Vis. Sci. (2009) 50(7):3404-3409.
Van Leeuwen, G. et al., "High-Flow-Velocity and Shear-Rate Imaging by use of Color Doppler Optical Coherence Tomography", Opt Lett 24, 1584-1586 (1999).

(56) References Cited

OTHER PUBLICATIONS

Von Ruckmann, A., et al., "Distribution of Fundus Autofluorescence with a Scanning Laser Ophthalmoscope," Br. J. Ophthalmol. 79, 407-412 (1995).
Wang, L.V., "Multiscale Photoacoustic Microscopy and Computed Tomogrpahy," Nature Photonics 3, 503-509 (2009).
Wang, L.V., "Tutorial on Photoacoustic Microscopy and Computed Tomography", IEEE Journal of Selected Topics in Quantum Electronics 14(1):171-179 (2008).
Wang, X. et al., "Noninvasive Laser-Induced Photoacoustic Tomography for Structural and Functional in vivo Imaging of the Brain", Nature Biotechnology 21, 803-806 (2003).
Webb, R.H. et al., "Confocal Scanning Laser Opthalmoscope," Applied Optics 26, 1492-1499 (1987).
Webb, R.H. et al., "Scanning Laser Ophthalmoscope," IEEE Trans. Biomed. Eng. BME-28, 488-492 (1981).
Wehbe, H. et al., "Automatic Retinal Blood Flow Calculation Using Spectral Domain Optical Coherence Tomography", Optics Express 15, 15193-15206 (2007).
White, B.R. et al., "In vivo Dynamic Human Retinal Blood Flow Imaging Using Ultra-High-Speed Spectral Domain Optical Doppler Tomography", Optics Express 11, 3490-3497 (2003).
Wild, S. et al., "Global Prevalence of Diabetes—Estimates for the Year 2000 and Projections for 2030", Diabetes Care 27, 1047-1053 (2004).
Williams, G.G. et al., "Single-Field Fundus Photography for Diabetic Ritinopathy Screening: A Report by the American Academy of Ophthalmology" Ophthalmology 111, 1055-62 (2004).
Wojtkowski, M. et al., "In vivo Human Retinal Imaging by Fourier Doman Optical Coherence Tomography," J. Biomedical Opt. 7, 457-463 (2002).
Wojtkowski, M. et al., "Ultrahigh-resolution, high-speed, Fourier domain optical coherence tomography and methods for dispersion compensation," Opt. Express, 2004, vol. 12, p. 2404.
Xie, Z. et al., "Laser-Scanning Optical-Resolution Photoacoustic Microscopy," Optics Letters 34, No. 12, 1771-1773, (2009).
Yakovlev, V.V. et al., "Stimulated Raman Photoacoustic Imaging", Under Review with Proc. Natl. Acad. Sci. USA. (2009).
Yazdanfar, S. et al., "In vivo Imaging of Human Retinal Flow Dynamics by Color Doppler Optical Coherence Tomography", Archives of Ophthalmolology 121, 235-239 (2003).
Yoshida, A., et al., "Retinal Blood-Flow Alterations During Progression of Diabetic-Retinopathy", Arch Ophthalmol-Chic 101, 225-227 (1983).
Yu, D.Y. et al., "Pathogenesis and Intervention Strategies in Diabetic Retinopathy" Clin Exp Ophthalmol 29, 164-166 (2001).
Zemp, R. et al., "Stochastic Explanation of Speckle Contrast Detection in Ultrasound-Modulated Optical Tomography", Phys Rev E 73,—(2006).
Zhang, H.F. et al., "An Automatic Algorithm for Skin Profile Detection in Photoacoustic Microscopy", Under Revision with Journal of Biomedical Optics (2009).
Zhang, H.F. et al., "Collecting Back-Reflected Photons in Photoacoustic Microscopy", Optics Express 18, 1278-1282 (2010).
Zhang, H.F. et al., "Functional Photoacoustic Microscopy for High-Resolution and Noninvasive in vivo Imaging," Nature Biotechnology, vol. 24, No. 7, pp. 848-851 Jul. 2006.
Zhang, H.F. et al., "Imaging of Hemoglobin Oxygen Saturation Variations in Single Vessels in vivo Using Photoacoustic Microscopy", Applied Physics Letters 90, 053901, 2007.
Zhang, H.F. et al., "In vivo Imaging of Subcutaneous Structures Using Functional Photoacoustic Microscopy", Nature Protocols 4, 797-804, (2007).
Zhang, H.F. et al., "In vivo Volumetric Imaging of Subcutaneous Microvasculature using Photoacoustic Microscopy", Optics Express 14, 9317-9323 (2006).
Zhang, H.F. et al., "Naturally Combined Photoacoustic Microscopy and Optical Coherence Tomography for Simultaneous Multimodal Imaging", 2009.
Zhang, E.Z. et al., "Multimodal photoacoustic and optical coherence tomography scanner using an all optical detection scheme for 3D morphological skin imaging," Biomedical Optics Express, Aug. 1, 2011, vol. 2, No. 6, pp. 2202-2215.
Zhang. H.F. et al., "Imaging acute thermal burns by photoacoustic microscopy," Journal of biomedical optics, 2006, vol. 11, p. 054033.
Zhange, E.Z. et al., "In vivo High-Resolution 3D Photoacoustic Imaging of Superficial Vascular Anatomy," Physics in Medicine and Biology 54, 1035-1046 (2009).
Zharov, V.P. et al., "In vivo Photoacoustic Flow Cytometry for Monitoring of Circulating Single Cancer Cells and Contrast Agents", Optics Letters 31, 3623-2325 (2006).
Zhou, Q.F. et al., "Design and Fabrication of PZN-7%PT Single Crystal High Frequency Angled Needle Ultrasound Transducers", IEEE Transactions on Ultrasonics, Ferroelectrics, and Frequency Control, 55, 1394-1399 (2008).
Zhou, Q.F. et al., "PMN-PT Single Crystal High Frequency Ultrasonic Needle Transducers for Pulsed Wave Doppler Application", IEEE Transactions on Ultrasonics, Ferroelectrics, and Frequency Control Vo 54, 668-675 (2007).
International Search Report and Written Opinion for Application No. PCT/US2010/027682 dated May 19, 2010 (7 pages).
International Preliminary Report on Patentability for Application No. PCT/US2010/027682 dated Sep. 20, 2011 (6 pages).
International Search Report and Written Opinion for Application No. PCT/US2010/027685 dated May 18, 2010 (9 pages).
International Preliminary Report on Patentability for Application No. PCT/US2010/027685 dated Sep. 20, 2011 (7 pages).
United States Patent Office Action for U.S. Appl. No. 12/726,172 dated Nov. 12, 2010 (14 pages).
United States Patent Office Notice of Allowance for U.S. Appl. No. 12/726,172 dated Jul. 26, 2011 (8 pages).
United States Patent Office Action for U.S. Appl. No. 12/726,176 dated Nov. 24, 2010 (13 pages).
United States Patent Office Notice of Allowance for U.S. Appl. No. 12/726,176 dated Mar. 31, 2011 (8 pages).
United States Patent Office Action for U.S. Appl. No. 12/726,182 dated Jun. 8, 2012 (13 pages).
United States Patent Office Action for U.S. Appl. No. 12/726,182 dated Nov. 27, 2012 (14 pages).
United States Patent Office Action for U.S. Appl. No. 12/726,186 dated May 11, 2012 (11 pages).
United States Patent Office Action for U.S. Appl. No. 12/726,186 dated Oct. 25, 2012 (14 pages).

* cited by examiner

FIG. 4A
OCT B-Scan 250

FIG. 4B
PAM B-Scan 270

FIG. 4C
Fused OCT & PAM 280

OPTICAL COHERENCE PHOTOACOUSTIC MICROSCOPY

RELATED APPLICATIONS

This application claims priority benefit to U.S. Provisional Application No. 61/497,323, filed Jun. 15, 2011, the entire contents of which are hereby incorporated by reference.

BACKGROUND

The present invention relates to optical coherence tomography (OCT) and photoacoustic microscopy (PAM).

SUMMARY

OCT and PAM are two microscopic three-dimensional non-invasive imaging modalities that are based on different contrast mechanisms. OCT is a low-coherent interferometer-based optical imaging modality that provides imaging of mainly the scattering properties of biological tissues. By using a broadband light source, OCT resolves the depth of a scatterer through coherence gating.

In contrast, PAM is an optical-absorption based imaging modality that detects laser-induced ultrasonic waves as a result of specific optical absorption. When short laser pulses irradiate biological tissues, optical energy is absorbed by substances like hemoglobin and melanin and converted to heat. Thermo-elastic expansions then occur, which lead to the generation of wideband ultrasonic waves. The ultrasonic waves are detected by an ultrasonic transducer and used to quantify the optical absorption properties of the sample. The waves may be used to form an image of the sample based upon the optical absorption contrast of elements of the sample, such as tissue of a biological sample.

Due to the different contrast mechanisms, OCT and PAM can provide different, but complementary, information of biological tissues. OCT images the microanatomy of a sample, such as a histology-like cross-sectional image of a retina. OCT can also measure blood flow velocity by measuring the Doppler effect impinged on the probing light. In contrast, PAM images a microvasculature and blood oxygenation by using multiple wavelength illumination.

Previously, light sources used in OCT and PAM were different. OCT generally uses near infrared, broadband and continuous light, such as produced by a superluminescent diode (SLD), or infrared, virtually continuous light, such as produced by a Ti:Sapphire laser with approximately 80 MHz pulse repetition rate. In contrast, PAM generally uses narrow band and pulsed lasers in the visible light spectrum targeting, for instance, the absorption of hemoglobin. Use of near infrared (NIR) light in OCT allows for deeper penetration depth than otherwise achievable using light in the visible spectrum. The selection of light wavelength in PAM, including whether visible light or NIR light, depends on the absorption spectrum of the targeted molecules. Additional information related to OCT and PAM imaging may be found in U.S. Pat. No. 8,025,406, the entire contents of which are hereby incorporated by reference.

Embodiments of the invention relate to systems and methods for optical coherence photoacoustic microscopy (OC-PAM), a multi-modal microscopic imaging modality that can simultaneously image the absorption and scattering contrasts of biological tissues non-invasively. OC-PAM uses one light source, such as a pulsed broadband laser or a swept laser that outputs pulsed swept laser light of a plurality of wavelengths in a short scan period (e.g., less than 10 nanoseconds (ns)), to simultaneously achieve both PAM functions, by detecting the absorption-induced photoacoustic waves, and OCT functions, by detecting the reflected light using an interferometer. In OC-PAM imaging, with each laser pulse, an A-scan is generated for both OCT and PAM, respectively. Additionally, OC-PAM imaging generates inherently registered PAM and OCT images, providing an ability to study the scattering and absorption of biological tissues.

Embodiments of the invention can be used for OC-PAM imaging of a biological sample, such as a human eye. For example, light of the OC-PAM microscopes disclosed herein may enter through a pupil and be directed to a retinal region of interest within an eye. Additionally, the systems and methods disclosed herein may be used to image various biological samples such as cells and molecules in suspension, physiological appendages, small animal organs (e.g., ears, skin, eyes, brain, internal organs, etc.) and human eyes and skin.

In another embodiment, the invention provides an optical coherence photoacoustic microscope including a light source that outputs light, a sample, a detector, a transducer, and an image processing module. The sample receives the light, which is scanned across the sample. The detector receives reflected light from the sample in response to the scanned light. The transducer is positioned to detect photoacoustic waves induced in the sample by the scanned light. The image processing module receives output from the transducer and the detector and generates a photoacoustic microscopy (PAM) image and an optical coherence tomography (OCT) image based on the received output from the detector and the transducer.

In another embodiment, the invention provides a method for optical coherence photoacoustic microscope. The method includes emitting light from a light source and scanning the light across a sample. A detector receives reflected light from the sample in response to the scanned light. The method further includes detecting, by a transducer, photoacoustic waves induced in the sample by the scanned light, and receiving, by an image processing module, output from the detector and the transducer. The image processing module generates a photoacoustic microscopy (PAM) image and an optical coherence tomography (OCT) image based on the received output from the detector and the transducer.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising," or "having" and variations thereof herein is meant to encompass the items listed thereafter and equivalents thereof as well as additional items. The terms "mounted," "connected," and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

It should be noted that a plurality of hardware and software based devices, as well as a plurality of different structural components may be utilized to implement the invention. Furthermore, and as described in subsequent paragraphs, the specific configurations illustrated in the drawings are intended to exemplify embodiments of the invention and that other alternative configurations are possible.

Figure 1:
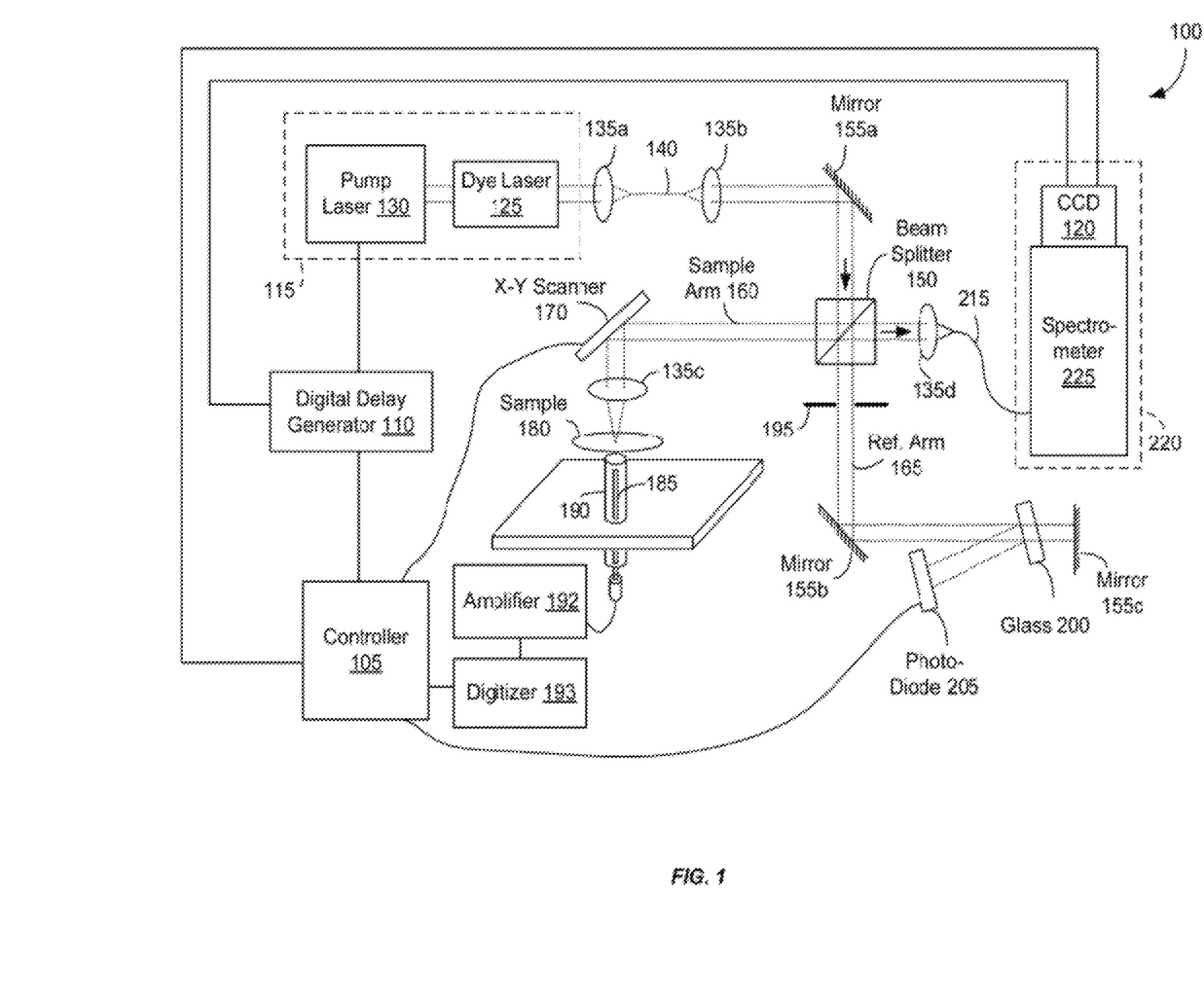
FIG. 1 illustrates an optical coherence photoacoustic microscopy (OC-PAM) microscope in a transmission mode according to embodiments of the invention.

FIG. 1 illustrates an optical coherence photoacoustic microscopy (OC-PAM) microscope 100 according to embodiments of the invention. The microscope 100 includes a controller 105 for providing a user interface for operating and viewing images generated by the microscope 100. The controller 105 may be implemented by hardware, software, or a combination thereof. For instance, the controller 105 may include one or more of a general purpose processing unit, a digital signal processor, a field programmable gate array (FPGA), an application specific integrated circuit (ASIC), and other processing devices operable to carry out the functions attributable to the controller 105 described herein. The controller 105 may further include a memory, or be coupled to a memory, that stores instructions executed by the controller 105 to carry out the aforementioned functions, may store data for the controller 105, such as image data, and may load data to the controller 105, such as program data, calibration data, etc. for use by the controller 105 during operation of the microscope 100. Additionally, the controller 105 may include user interface components, such as a display, a graphical user interface (GUI), keyboard, mouse, touch screen, etc., to allow a user to control and interact with the microscope 100, and to view resulting images.

The controller 105 is coupled to and provides signals to a digital delay generator 110. In response to the signals from the controller 105 and a clock output, such as a clock of an analog output, the digital delay generator 110 triggers a laser 115 to output pulses. The digital delay generator 110 is also coupled to a charge coupled device (CCD) camera 120 to trigger image capture by the CCD camera 120 with appropriate timing. In some embodiments, a complementary metal-oxide-semiconductor CMOS camera is used in place of the CCD camera 120.

The laser 115 includes a broadband dye laser 125 pumped by a pump laser 130. The pump laser 130 is a frequency-double Q-switched Nd:YAG (neodymium-doped yttrium aluminum garnet) laser. For instance, the pump laser 130 may be a PSOT-10-100-532 laser sold by Elforlight Ltd., which produces a 532 nm, 10 μJ/pulse pulse with a 2 ns pulse duration, 30 kHz pulse repetition rate. The output light of the laser 115 has a center wavelength of 580 nm and a bandwidth of 20 nm with, for instance, a 5 kHz pulse repetition rate. The particular laser output may be varied depending on the application. Generally, as the center wavelength of the laser output increases, the bandwidth also increases. For example, when the laser output has a center wavelength of 830 nm, the bandwidth may be 50 nm (i.e., 830 nm+/−25 nm); and when the laser output has a center wavelength of 1000 nm, the bandwidth may be 100 nm (i.e., 830 nm+/−50 nm). In general, the square of the center wavelength divided by the bandwidth $$\left(\text{i.e., } \frac{CenterWavelength^2}{Bandwidth}\right)$$

is within an approximate range of about 10,000 to 20,000, although, in certain embodiments, the ratio may be higher than 20,000 or lower than 10,000. For example, $$\frac{830^2}{50} = \frac{688900}{50} = 13,778.$$

In some instances, the spectrum of the laser pulses from the laser 115 has a relatively high noise level, which may reduce the quality of the OCT images acquired by the microscope 100. However, this reduction in quality may be somewhat offset by using pulsed light with stable spectral performance.

In some embodiments, the laser 115 generates output using components different than the pump laser 130 and dye laser 125. Furthermore, in some embodiments, the laser 115 is a swept laser source that outputs pulsed swept laser light of a plurality of wavelengths, which are swept in a scan period shorter than 10 ns. Alternatively, the laser 115 may be a pulsed supercontinuum light source, a pulsed broadband superluminescent diode (SLD), or a broadband Ti:Sapphire laser. Additionally, in some embodiments, the light spectrum emitted by the laser 115 may tend closer to or include near infrared (NIR) wavelengths to achieve better imaging depth and ophthalmic applications. The particular wavelengths emitted by the laser 115 may vary depending on the targeted absorber in a sample to be imaged.

Figure 2A:
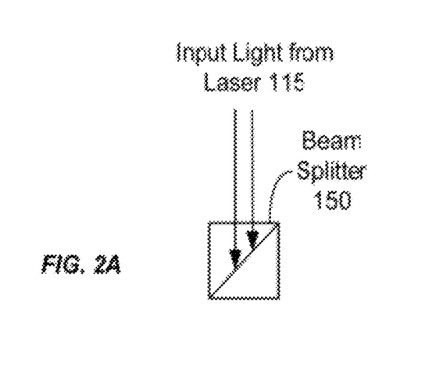
FIGS. 2A-D illustrate light passing through the beam splitter 150 at various stages of OC-PAM.
Figure 2B:
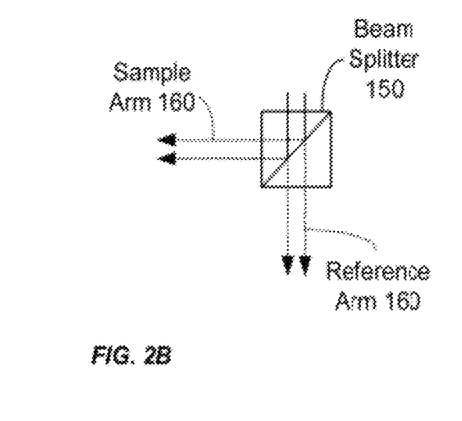

The light output by the laser 115 is focused by a lens 135 on a single mode optical fiber (SMF) 140. The SMF 140 outputs the light towards a lens 145, which collimates the light and directs it to a beam-splitter cube 150 via a mirror 155a. The light received by the beam-splitter cube 150 is split into sample arm light 160 and reference arm light 165, which is more clearly illustrated in FIGS. 2A-B. The sample arm light 160 is directed by an x-y scanner 170, under control of the controller 105, towards a lens 135c. The lens 135c focuses the sample arm light 160 onto a sample 180.

In response to the sample arm light 160, the sample 180 (a) reflects a portion of the light and (b) absorbs a portion of the light. The absorbed portion of light is converted to heat and causes thermo-elastic expansions to occur in the sample 180. The thermo-elastic expansions generate wideband ultrasonic waves, which are detected by an ultrasonic transducer 185. The ultrasonic transducer 185 is a needle ultrasonic transducer (30 MHz; bandwidth: 50%; active element diameter: 0.4 mm), which is inserted into a plastic tube 190 filled with ultrasonic gel. The tube 190 and transducer 185 are placed under and in physical contact with the sample 180. The transducer 185 outputs an analog signal to an amplifier 192, which outputs the signal, amplified, to a digitizer 193. The digitizer 193 is coupled to the controller 105 to provide the controller 105 with the digitized, amplified signal from the transducer 185. The distance between the ultrasonic transducer 185 and sample 180 in the application illustrated in FIG. 1 is approximately 6 mm. In other embodiments, alternate transducers configurations are used in place of the transducer 185 and/or tube 190, and may be positioned in alternate locations with respect to the sample 180, such as above the sample 180. In some embodiments, one or more of the ultrasonic transducer 185, amplifier 192, and digitizer 193 are combined into an integrated unit. In some embodiments, the transducer 185 is integrated into a contact lens for placement directly on the eye to be scanned.

After the beam splitter 150 splits the light into the sample arm 160 and the reference arm light 165, the reference arm light 165 passes through an iris 195 and is reflected by a mirror 155b towards a mirror 155c. The reference arm light 165 reaches a glass plate 200, which allows the majority of the reference arm light 165 to pass through to the mirror 155c, but reflects a portion of the reference arm light 165 towards a photo diode 205. The photo diode 205 outputs a signal to the controller 105 indicating the receipt of the reflected reference arm light 165. The signal from the photo diode 205 triggers capture by the controller 105 of the digitized, amplified transducer data emitted by the digitizer 193.

The glass plate 200 is a BK7 glass plate, which is used to compensate for the group-velocity dispersion mismatch between the sample arm 160 and the reference arm 165. In some embodiments, a different glass plate is used in the microscope 100.

Figure 2C:
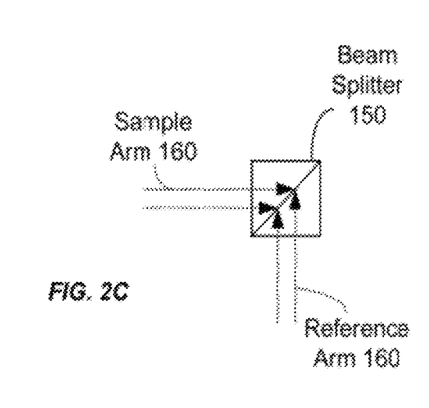
Figure 2D:
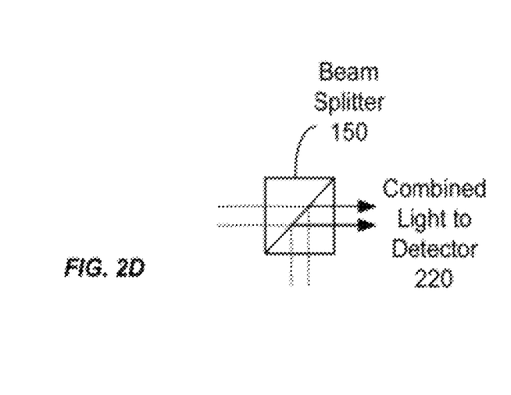

The reference arm light 165 that passes through the glass plate 200 is reflected by the mirror 155c back towards the glass plate 200 and mirror 155b. The majority of the reflected light is passed through the glass plate 200 and proceeds to the mirror 155b, which reflects the reference arm light 165 through the iris 195 on route to the beam splitter 150. Simultaneously, the light reflected by the sample 180 passes back through the lens 135c and is reflected by the x-y scanner 170 towards the beam splitter 150. The returning sample arm light 160 then passes through the beam splitter 150 while the returning reference arm light 165 is reflected by the beam splitter 150, resulting in the returning sample arm light 160 and reference arm light 165 being combined by the beam splitter 150. FIGS. 2C-D illustrate the combination of the sample arm light 160 and reference arm light 160 by the beam splitter 150. In some embodiments, in place of the beam splitter 150, one or more fiber couplers may be used to split and combine the sample arm light 160 and reference arm light 165. The combined light is then focused by a lens 135d on a single mode fiber 215. The single mode fiber 215 is a fiber optic medium that transmits the light to a detector 220 that includes a spectrometer 225 and the CCD camera 120. The combined sample arm light 160 and reference arm light 165 provide an interference pattern, as each arm has traveled approximately the same optical distance.

The spectrometer 225 includes a diffractive grating, such as a transmission grating with 1800 line pairs per millimeter (lp/mm) and an imaging lens (e.g., having f=150 mm). The diffractive grating disperses the light from the single mode fiber 215 as a line spectrum on the imaging lens, which focuses the line spectrum on the CCD camera 120. The CCD camera 120 is a line scan type, such as an Aviiva-SM2-CL-2010, with 2048 pixels operating in 12-bit mode, e2V. As previously noted, the digital delay generator 110 provides a triggering signal to trigger image capture by the CCD camera 120 when the dispersed light reaches the CCD camera 120. The exposure time of the camera is based on the pulse width of the light emitted by the laser 115 and is, generally, approximately the same time length as the period of the pulse width of the light. The shutter may be open for more or less time than the period of the pulse width of the laser 115. The effective exposure time is the time that the laser is emitting light and the shutter of the camera 120 is open.

The microscope 100 scans an area (x by y) of the sample 180, one (x,y) coordinate point at a time. The image data captured by the CCD camera 120 form the OCT images, while the transducer data obtained by the transducer 185 form the PAM information.

Figure 3A:
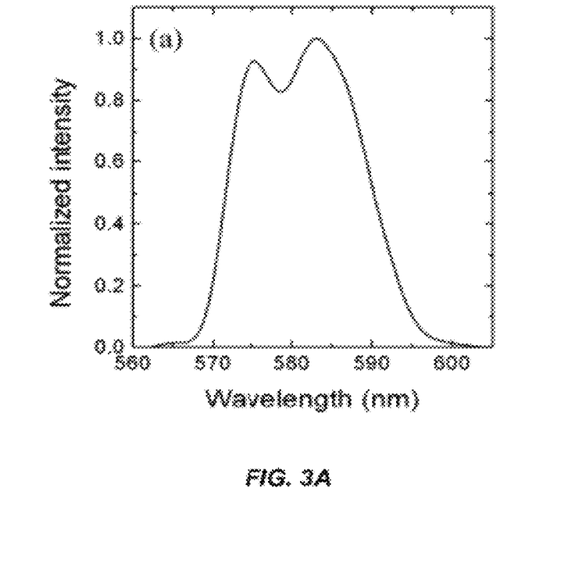
FIGS. 3A-B illustrate examples of optical coherence tomography (OCT) image data.
Figure 3B:
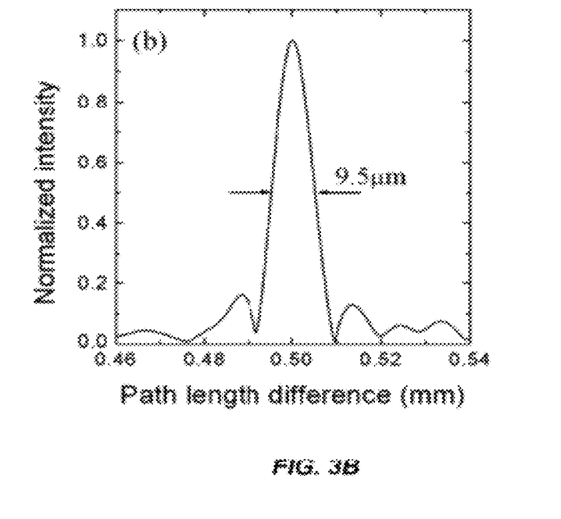

With respect to OCT imaging, for each scanned point on the sample 180, the CCD camera 120 captures one line of image data on the CCD camera 120 for each coordinate point (an "A-scan"). FIGS. 3A-B illustrate low-pass filtered image data obtained by the CCD camera 120 based on the illumination of a single point on the sample 180. FIG. 3A illustrates the normalized intensity for the light received by the CCD camera 120 at the various wavelengths of the light as dispersed by the spectrometer 225. FIG. 3B illustrates a calculated point-spread-function (PSF) of the OCT data. In the example illustrated in FIGS. 3A-B, the sample 180 was a mirror, the path length difference was set to 0.5 mm, and the exposure time of the CCD camera 120 was set to 10 μs. As shown in FIG. 3B, the measured depth resolution is 9.5 μm in air.

A cross-sectional tomograph (B-scan) may be achieved by laterally combining a series of the A-scans. Thus, after scanning the x by y area of the sample 180, three-dimensions of image data have been captured corresponding to the x-dimension of the sample 180, the y-dimension of the sample 180, and the z-dimension (depth) of the sample 180. The z-dimension is based on the spectral information, including the intensity of the various wavelengths of light received by the CCD camera 120.

Figures 4A, 4B:
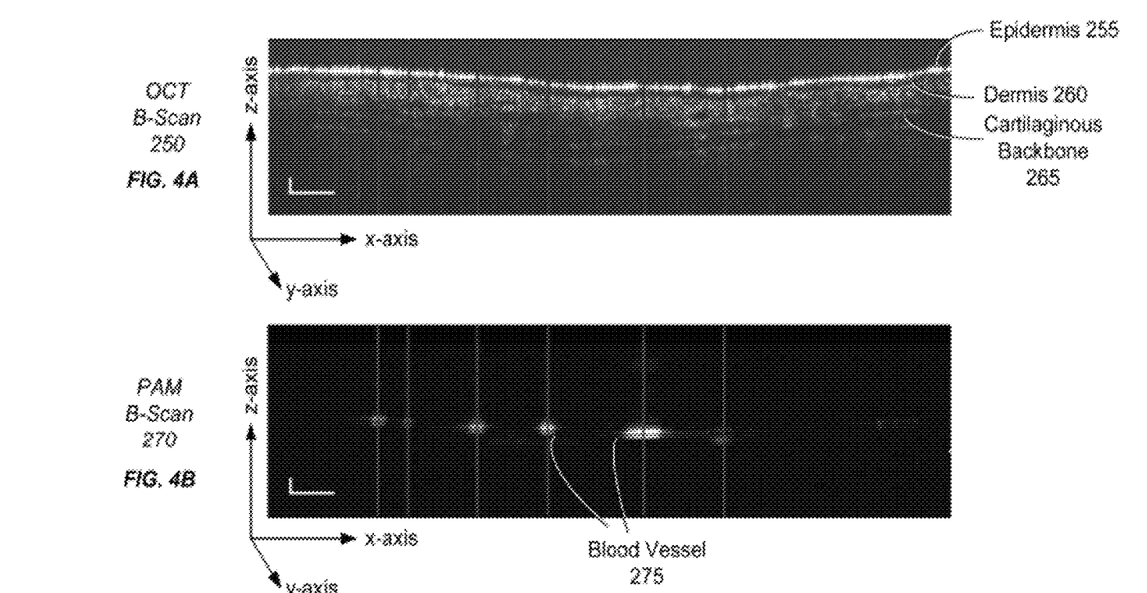
FIG. 4A illustrates an OCT B-scan of a mouse ear generated with the OC-PAM microscope of FIG. 1.
FIG. 4B illustrates a photoacoustic microscopy (PAM) B-scan simultaneously generated with the OC-PAM microscope of FIG. 1.

FIG. 4A illustrates a B-scan OCT image 250 generated by the OCT imaging components of the microscope 100. The OCT image 250 shows a cross-section of a portion of the mouse ear. In the OCT image 250, the depth resolution is sufficient to resolve different anatomical features including the epidermis 255, dermis 260, and cartilaginous backbone 265 of the sample 180, which is a mouse ear. In this example, the OCT image reaches about half of the thickness of the mouse ear.

With respect to PAM imaging, for each scanned point on the sample 180, the transducer 185 captures ultrasound data over time to generate an A-scan image which indicates the depth of various components of the sample 180. The series of A-scan images are laterally combined to form a B-scan image having three-dimensions of ultrasound data corresponding to the x-dimension of the sample 180, the y-dimension of the sample 180, and the z-dimension (depth) of the sample 180. The z-dimension data is based on the timing of the ultrasonic waves received by the transducer.

FIG. 4B illustrates a B-scan PAM image 270 generated by the PAM imaging components of the microscope 100. The PAM image 270 shows a cross section of a portion of a mouse ear, with the cross section of blood vessels 275 of the mouse ear appearing as clusters of high amplitude ultrasonic signals. However, information about the anatomy of the tissue is not present where no significant absorption of the sample arm light 160 occurred.

For example, to generate the B-scan image data for either of the B-scan OCT image 250 or the B-scan PAM image 270, while the sample arm light 160 is scanned in the one dimension (e.g., x=0 to n), the other dimension is fixed (e.g., y=0). For each x-position, an A-scan is generating, resulting in a vertical line of image data. To form the B-scan image 250 or 270, the series of vertical lines of image data are combined. Since both the OCT image 250 and PAM image 270 are generated from the same photons, they are inherently and precisely co-registered in the lateral directions (e.g., the x- and y-dimensions), which are determined by the optical scanning. In the depth direction, however, registration of the two imaging modes is not automatic. One technique for image registration in the depth direction is to first establish a relationship of the two images in the depth direction by, for instance, imaging a flat absorbing surface such as black tape. The PAM image will then be scaled and interpolated accordingly and then fused with the OCT image.

Figure 4C:
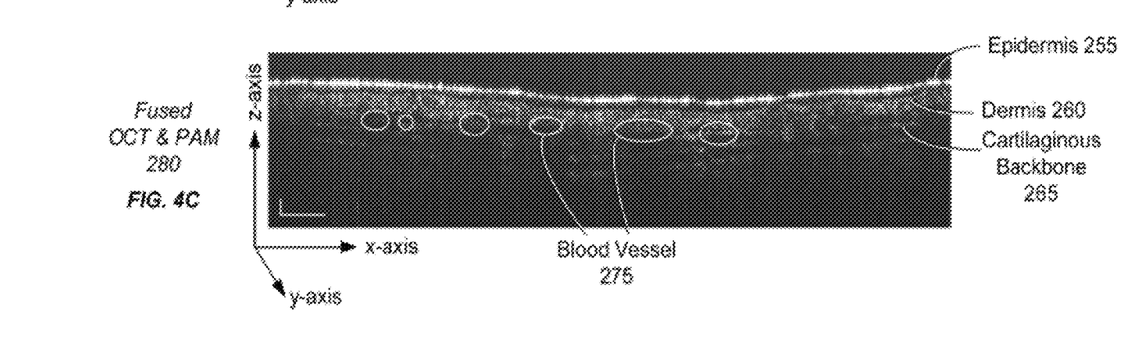
FIG. 4C illustrates a fused PAM B-scan and OCT B-scan generated with the OC-PAM microscope of FIG. 1.

FIG. 4C illustrates an example of a fused OCT and PAM image 280, which includes a combination of the OCT image 250 and PAM image 270. The fused image 280 is a cross sectional view of the scanned portion of the mouse ear showing the blood vessels 275 of the PAM image 270 and the epidermis 255, dermis 260, and cartilaginous backbone 265 of the OCT image 250.

Figure 5:
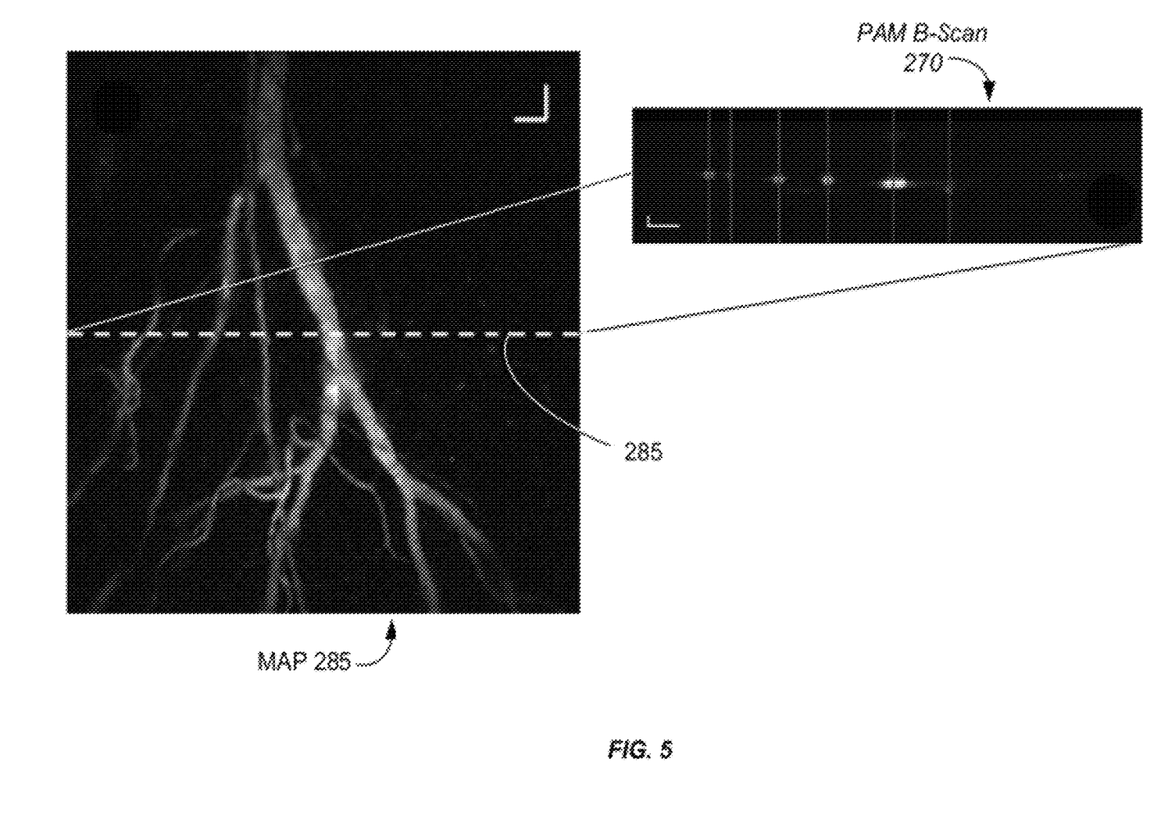
FIG. 5 illustrates a maximum amplitude projection (MAP) image formed from PAM B-scans generated with the OC-PAM microscope of FIG. 1.

FIG. 5 illustrates a maximum-amplitude-projection (MAP) 285 of a 3D PAM dataset generated by the microscope 100. A series of B-scans generated by the PAM components of the microscope 100 are stacked to generate the MAP 285. The MAP 285 shows a top-down view of the sample 180, i.e., as if viewing the sample 180 from a position of the lens 135c above the sample 180. As shown in FIG. 5, the B-scan 270 of FIG. 4B is a portion of the MAP 285 centered at the horizontal line 290. The B-scan 270, along with a series of additional B-scans, are stacked such that the blood vessels 275 of multiple B-scans combine to form the blood vessel 290 shown in FIG. 5. The PAM dataset making up the MAP 285 includes 256×256 PAM A-scans covering an area of 2.6×2.6 mm$^2$.

Figure 6:
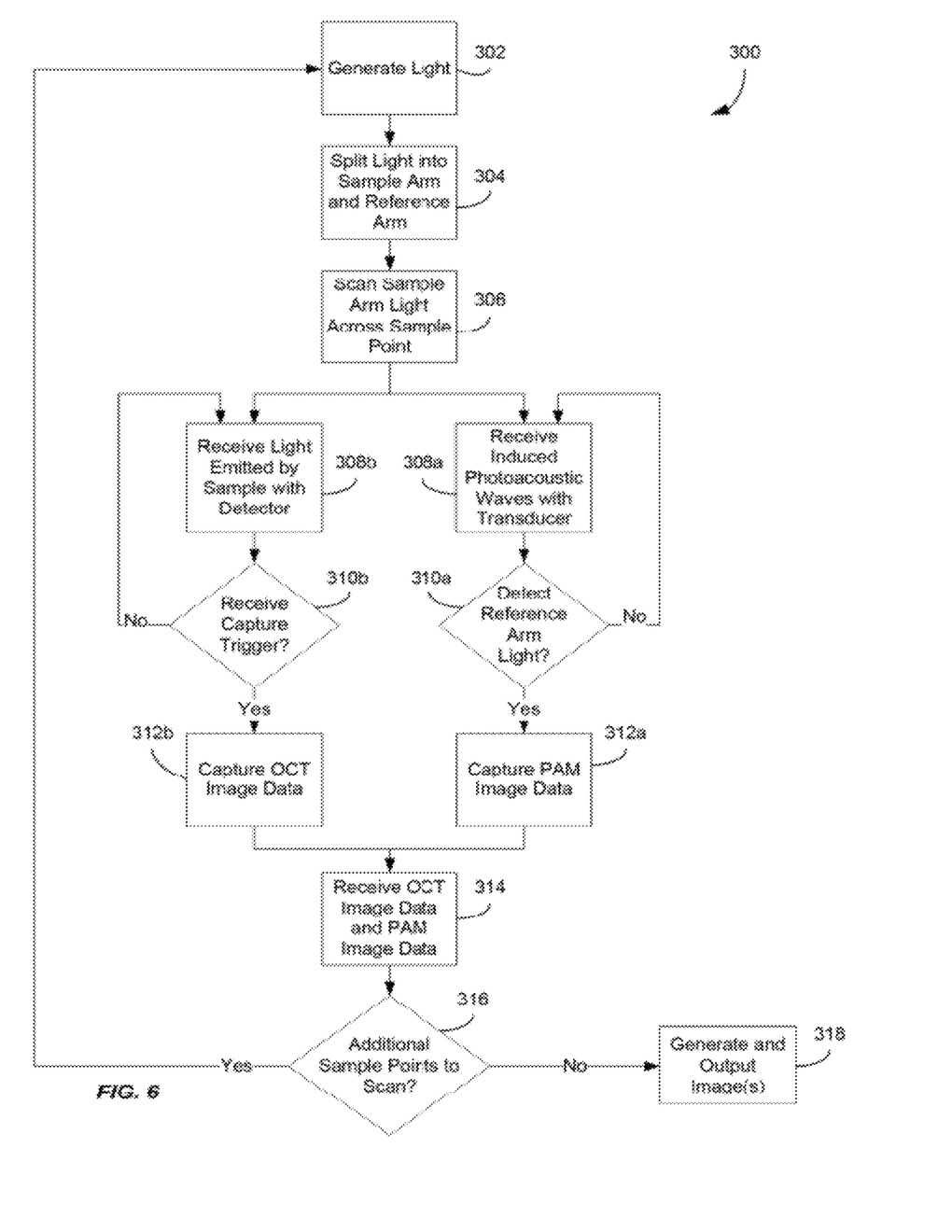
FIG. 6 illustrates an OC-PAM method for generating OCT and PAM image data using a single light source.

FIG. 6 illustrates a method 300 of generating OC-PAM images with a single light source using, for instance, the microscope 100. Accordingly, the method 300 is described with reference to the microscope 100; however, other microscopes using a single light source may also perform the steps of method 300. In step 302, the laser 115 emits broadband pulsed light towards the beam splitter 150. In step 304, the beam splitter 150 splits the emitted broadband pulsed light into the sample arm light 160 and the reference arm light 165. In step 306, the x-y scanner 170 directs the sample arm light 160 to a point on the sample 180. A portion of the sample arm light 160 is absorbed by the sample 180 and converted into photoacoustic waves, and another portion of the sample arm light 160 is reflected by the sample 180 back toward the beam splitter 150.

In step 308a, the photoacoustic waves generated by the sample 180 are received by the transducer 185. Meanwhile, a portion of the reference arm light 165 is reflected off of the glass 200 and is received by the photodiode 205 in step 310a, which, in step 312a, triggers the controller 105 to capture the PAM data received by the transducer 185. Essentially simultaneously with step 308a, in step 308b, the beam splitter 150 combines the portion of the sample arm light 160 reflected by the sample 180 with the reference arm light 165 returning from mirrors 155b and 155c, and provides the combined light to the detector 220. In step 310b, the detector 220 is triggered by the digital delay generator 110 and, in response, in step 312b, the detector 220 captures OCT image data generated by the combined light reaching the detector 220. The detector 220 then provides the OCT image data to the controller 105. In step 314, the OCT image data and PAM image data captured in step 312 are received by an imaging module (not shown) of the controller 105 for processing and may be saved in a memory of the controller 105.

In step 316, the controller 105 determines whether additional portions of the sample 180 remain to be scanned. If additional portions remain, the controller 300 returns to step 302 and proceeds to generate additional OCT and PAM data for the next point on the sample. Once all of the sample points of the sample 180 have been scanned as determined in step 316, the controller 105 proceeds to step 318 for image processing of the OCT and PAM data. For instance, images such as shown in FIG. 3A to 5 are generated by the imaging module of the controller 105 and saved in a memory of the controller 105 or output by the controller 105 to a display for viewing, to another computing device for further processing or display, to a remote device over a network, to a remote storage device on a network, or to another device.

Figure 7:
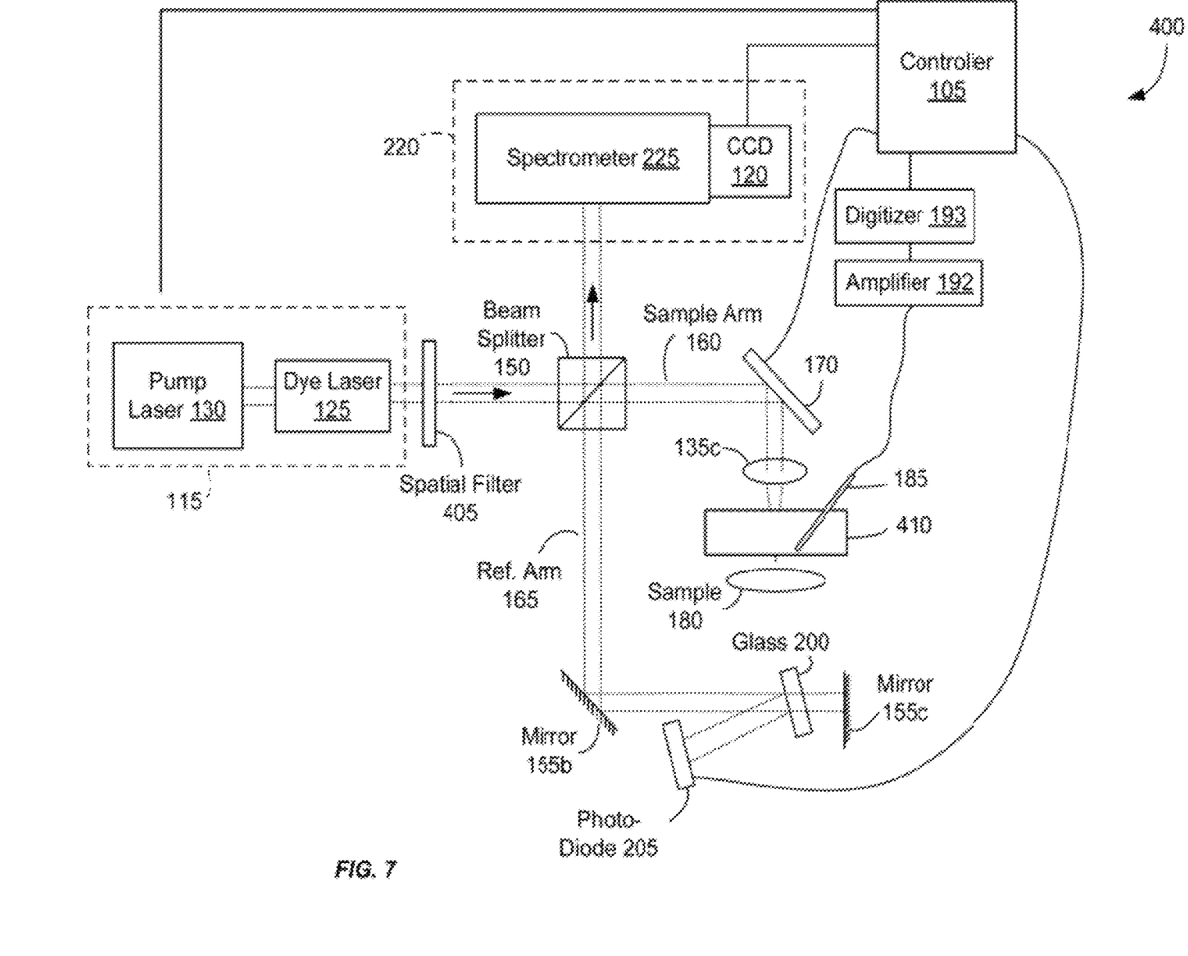
FIG. 7 illustrates an OC-PAM microscope in a relction mode according to embodiments of the invention.

FIG. 7 illustrates an OC-PAM microscope 400 having an alternate arrangement. The microscope 400 has several components similar to the microscope 100 and such components are like-numbered. Light emitted from the laser 115 is filtered by spatial filter 405 and collimated before reaching the beam splitter 150, which, like the microscope 100, splits the emitted light into the sample arm light 160 and reference arm light 165. The microscope 400 functions with respect to the reference arm light 165 in a manner similar to the microscope 100. The sample arm light 160 is focused by the lens 135c and scanned across the sample 180 via the x-y scanning mirror 170. In the microscope 400, the transducer 185 is positioned above the sample 180, rather than below the sample as in the microscope 100. Additionally, as an alternate to the tube 190 and ultrasound gel of the microscope 100, the transducer 185 of the microscope 400 is positioned in a water tank 410. Like the microscope 100, the microscope 400 captures OCT data with the detector 220 and PAM data with the transducer 185, which are generated based on the same photons output by the laser 115 and are, therefore, inherently and precisely co-registered in the lateral directions.

The microscopes 100 and 400 of FIGS. 1 and 7, respectively, include an x-y scanner 170 to scan the light across the sample 180. In some embodiments, however, the light from the laser 115 remains fixed while the sample 180, which is on a controlled scanning platform, is moved by the platform to scan the light across the sample 180. For instance, in these embodiments, the x-y scanner 170 may be replaced by a fixed mirror or may be held in a fixed position during a scan.

Thus, the invention provides, among other things, an OC-PAM system and method for simultaneously capturing OCT and PAM image data of a sample induced by a single light source.

In one embodiment, the invention provides an optical coherence photoacoustic microscope. The microscope includes a light source that outputs broadband pulsed light, a scanner, a Michelson interferometer with a spectrometer as a light detector, an ultrasonic transducer, and an image processing module. The scanner receives the light and scans the light across a sample. The spectrometer in a detection arm of the interferometer receives back-scattered light from the sample in response to the scanned light, which interferes with reflected light from a reference arm of the interferometer. The transducer detects photoacoustic waves induced in the sample by the scanned light in a transmission mode, where the transducer is placed on a side of the sample opposite the scanning light. The image processing module receives output from the spectrometer and the ultrasonic transducer and generates an optical coherence tomography (OCT) image and a photoacoustic microscopy (PAM) image based on the received output from the spectrometer and the transducer.

In another embodiment, the invention provides a method for optical coherence photoacoustic microscopy. In the method, broadband pulsed light is emitted from a light source and coupled into a source arm of a Michelson interferometer. The light is scanned across a sample. A spectrometer in a detection arm of the interferometer receives a combination of light back-scattered from the sample in response to the scanned light and light reflected from a reference arm of the interferometer. An ultrasonic transducer detects photoacoustic waves induced in the sample by the scanned light in a reflection mode, where the transducer is placed on a same side of the sample as the scanning light. An image processing module receives output from the spectrometer and the transducer and generates a photoacoustic microscopy (PAM) image and an optical coherence tomography (OCT) image based on the received output from the transducer and the spectrometer.

The systems and methods described herein may be used for the diagnosis and evaluation of age-related macular degeneration, geography atrophy, diabetic retinopathy, premature retinopathy, glaucoma, ocular tumors, retinal edema, retinal detachment, several types of ischemic retinopathy, and brain disorders. The systems and methods may further be used to monitor therapy on retinal diseases that use nano-particles and to provide therapy whereby the photons from the laser 115 are absorbed by the nano-particles to trigger a therapeutic reaction. Additionally, OC-PAM imaging may be used to diagnose diseases that may be diagnosed through morphology and functions of the retinal vessels, such as a stroke and Alzheimer's disease. Various features and advantages of the invention are set forth in the following claims.

What is claimed is:

1. An optical coherence photoacoustic microscope comprising:
   a light source that outputs light of a single center wavelength;
   a scanner that scans the output light of the single center wavelength across a sample by moving at least one of the sample and the light relative to the other of the sample and the light;
   a detector that receives reflected light from the sample in response to the scanned light;
   a transducer positioned to detect photoacoustic waves induced in the sample by the scanned light; and
   an image processing module that receives output from the transducer and the detector and that generates a photoacoustic microscopy (PAM) image and an optical coherence tomography (OCT) image based on the received output.

2. The optical coherence photoacoustic microscope of claim 1, wherein the light source is one of a pulsed broadband laser that outputs pulsed broadband light and a swept laser source that outputs pulsed swept laser light of a plurality of wavelengths, wherein the wavelengths are swept in a scan period shorter than 10 nanoseconds.

3. The optical coherence photoacoustic microscope of claim 1, wherein the image processing module further fuses together the PAM image and the OCT image to form a fused image.

4. The optical coherence photoacoustic microscope of claim 1, further comprising a beam splitter that splits the light into sample arm light and reference arm light.

5. The optical coherence photoacoustic microscope of claim 4, wherein the light received by the sample is the sample arm light.

6. The optical coherence photoacoustic microscope of claim 5, wherein the sample arm light passes through an optical system including a lens and a mirror.

7. The optical coherence photoacoustic microscope of claim 4, further comprising:
   a plate that partially reflects and partially transmits the reference arm light; and
   a photodiode that detects the reference arm light reflected by the plate and that outputs a trigger signal to initiate data acquisition.

8. The optical coherence photoacoustic microscope of claim 7, wherein the plate is a glass plate.

9. The optical coherence photoacoustic microscope of claim 7, wherein the reflected light received by the detector further includes the reference arm light transmitted by the plate.

10. The optical coherence photoacoustic microscope of claim 4, wherein the beam-splitter is one of fiber-based and free-space-based.

11. The optical coherence photoacoustic microscope of claim 1, wherein the detector includes
    a spectrometer, which receives the reflected light from the sample in response to the scanned light; and
    a camera that captures the reflected light received by the spectrometer and provides the output to the image processing module.

12. The optical coherence photoacoustic microscope of claim 1, wherein the detector includes
    a balanced photo-detector; which receives the reflected light from the sample in response to the scanned light; and
    a digitizer that captures the reflected light received by the balanced photo-detector and provides the output to the image processing module.

13. The optical coherence photoacoustic microscope of claim 1, wherein the light is scanned across the sample via an x-y scanner.

14. The optical coherence photoacoustic microscope of claim 1, wherein the transducer is positioned in a reflective configuration, whereby the transducer is on a laser receiving side of the sample.

15. The optical coherence photoacoustic microscope of claim 1, wherein the transducer is positioned in a transmission configuration, whereby the transducer is on a second side opposite the laser receiving side.

16. A method for optical coherence photoacoustic microscopy comprising:
   emitting light of a single center wavelength from a light source;
   scanning the light of the single center wavelength across a sample by moving at least one of the sample and the light relative to the other of the sample and the light;
   receiving, by a detector, reflected light from the sample in response to the scanned light;
   detecting, by a transducer, photoacoustic waves induced in the sample by the scanned light;
   receiving, by an image processing module, output from the transducer and the detector; and
   generating, by the image processing module, a photoacoustic microscopy (PAM) image and an optical coherence tomography (OCT) image based on the received output.

17. The method of claim 16, wherein the light source is one of a pulsed broadband laser that outputs pulsed broadband light and a swept laser source that outputs pulsed swept laser light of a plurality of wavelengths swept in a scan period shorter than 10 nanoseconds.

18. The method of claim 17, wherein the light source is the swept laser source and the detected photoacoustic waves have energy from the sum of the pulsed swept laser light of the plurality of wavelengths in the scan period.

19. The method of claim 16, further comprising fusing together the PAM image and the OCT image to form a fused image.

20. The method of claim 16, further comprising splitting, via a beam splitter, the light into sample arm light and reference arm light.

21. The method of claim 20, wherein the light scanned across the sample is the sample arm light.

22. The method of claim 20, further comprising transmitting the sample arm light through an optical system including a lens and a mirror on route to the sample.

23. The method of claim 20, further comprising:
   partially reflecting and partially transmitting the reference arm light using a plate;
   detecting, with a photodiode, the reference arm light reflected by the plate; and
   outputting, with the photodiode, a trigger signal to initiate data acquisition.

24. The method of claim 23, further comprising combining the reflected light, before reaching the detector, with the reference arm light partially transmitted by the plate.

25. The method of claim 16, wherein the receiving, by the detector, includes
   receiving, by a spectrometer, the reflected light from the sample in response to the scanned light; and
   capturing, by a camera, the reflected light received by the spectrometer.

26. The method of claim 16, wherein the receiving, by the detector, includes
   receiving, by a balanced photo-detector; the reflected light from the sample in response to the scanned light; and
   capturing, by a digitizer, the reflected light received by the balanced photo-detector.

27. The method of claim 16, further comprising establishing a depth relationship between the PAM image and the OCT image.

28. The method of claim 16, wherein scanning the light across the sample includes scanning the light via an x-y scanner that directs the light.

29. The method of claim 16, further comprising positioning the transducer in a reflective configuration, whereby the transducer is on a laser receiving side of the sample.

30. The method of claim 16, further comprising positioning the transducer in a transmission configuration, whereby the transducer is on a second side opposite the laser receiving side.

* * * * *

UNITED STATES PATENT AND TRADEMARK OFFICE
CERTIFICATE OF CORRECTION

PATENT NO. : 9,442,095 B2
APPLICATION NO. : 13/524813
DATED : September 13, 2016
INVENTOR(S) : Shuliang Jiao and Hao Zhang It is certified that error appears in the above-identified patent and that said Letters Patent is hereby corrected as shown below:

In the Specification

Column 1, Line 11 between the paragraphs for "Related Application" and "Background" please add
--STATEMENT REGARDING FEDERALLY SPONSORED RESEARCH FOR DEVELOPMENT
This invention was made with government support under 1 RC4 EY021357 (Subcontract No. 2791031 Board of Regents of the University of Wisconsin Systems) and 7 R21 EB008800-02 awarded by the National Institutes of Health. The government has certain rights in the invention.--

Signed and Sealed this
Sixth Day of June, 2017

Michelle K. Lee
*Director of the United States Patent and Trademark Office*